(12) United States Patent
Tsujimoto et al.

(10) Patent No.: US 7,097,999 B2
(45) Date of Patent: Aug. 29, 2006

(54) METHOD FOR PRODUCING TARGET SUBSTANCE USING MICROORGANISMS WITH REDUCED INTERACTIONS BETWEEN MALK AND IIA$^{GLC}$

(75) Inventors: Nobuharu Tsujimoto, Kawasaki (JP); Tomoko Suzuki, Kawasaki (JP); Hisao Ito, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 429 days.

(21) Appl. No.: 10/121,693

(22) Filed: Apr. 15, 2002

(65) Prior Publication Data

US 2003/0077764 A1 Apr. 24, 2003

(30) Foreign Application Priority Data

May 2, 2001 (JP) .............................. 2001-135517

(51) Int. Cl.
*C12P 1/00* (2006.01)
*C12P 13/04* (2006.01)

(52) U.S. Cl. ...................... 435/41; 435/106; 435/115; 435/108

(58) Field of Classification Search ................. 435/41, 435/106, 115, 108
See application file for complete search history.

(56) References Cited

U.S. PATENT DOCUMENTS 4,346,170 A 8/1982 Sano et al.

OTHER PUBLICATIONS

Ehrmann et al. Identification of Endogenous Inducers of the mal Regulon in Escherichia coli. J. Bacteriol. (1987) 169(8): 3539-3545.*

J. Monod, Growth, vol. 11, pp. 223-289, "The Phenomenon of Enzymatic Adaptation and its Bearings on Problems of Genetics and Cellular Differentiation", 1947.

P. W. Postma, et al., Escherichia Coli and Salmonella Cellular and Molecular Biology, Second Edition, vol. 1, pp. 1149-1174, "Phosphoenolpyruvate Carbohydrate Phosphotransferase Systems" 1996.

D.A. Dean, et al., Journal of Biological Chemistry, vol. 265, No. 34, pp. 21005-21010, "Regulation of the Maltose Transport System of *Escherichia Coli* by the Glucose-Specific Enzyme III of the Phosphoenolpyruvate-Sugar Phosphotransferase System", Dec. 5, 1990.

S. Kuhnau, et al., Journal of Bacteriology, vol. 173, No. 7, pp. 2180-2186, "The Activities of the *Escherichia Coli* Malk Protein in Maltose Transport, Regulation, and Inducer Exclusion can be Seperated by Mutations", Apr. 1991.

G. Q. Zeng, et al., Res. Microbiol., vol. 143, pp. 251-261, "Mutational Analysis of the Enzyme III$^{Glc}$ the Phosphoenolpyruvate Phosphotransferase System in *Escherichia Coli*", 1992.

* cited by examiner

*Primary Examiner*—Rebecca E. Prouty
*Assistant Examiner*—Iqbal Chowdhury
(74) *Attorney, Agent, or Firm*—Cermak & Kenealy, LLP; Shelly Guest Cermak

(57) ABSTRACT

The present invention describes a method for producing a target substance by utilizing a microorganism comprising culturing the microorganism in a medium, allowing the target substance to accumulate, and collecting the target substance from the medium. Also the microorganism used in the present invention is a mutant strain whereby maltose assimilation is controlled by the interaction between IIA$^{Glc}$ protein of glucose PTS and MalK.

5 Claims, 3 Drawing Sheets

METHOD FOR PRODUCING TARGET SUBSTANCE USING MICROORGANISMS WITH REDUCED INTERACTIONS BETWEEN MALK AND IIA$^{GLC}$

BACKGROUND OF THE INVENTION

1. Field of the Invention

The present invention relates to a method for producing a target substance by using a microorganism, more precisely, means for improving productivity of a substance that is an ultimate target product in a method for producing a target substance such as L-amino acids, antibiotics, vitamins, growth factors and bioactive substances by using a microorganism.

2. Description of the Related Art

As typical methods for producing substances by using microorganisms, there are known methods for producing L-amino acids by fermentation. L-amino acids are used not only as seasonings and foodstuffs but also as components of various nutritional mixtures for medical purposes. Furthermore, they are used as additives for animal feed, reagents in drug manufacturing industry and chemical industry and growth factors for production of L-amino acids such as L-lysine and L-homoserine by use of a microorganism. As microorganisms that can produce L-amino acids by fermentation, there are known coryneform bacteria, *Escherichia* bacteria, *Bacillus* bacteria, *Serratia* bacteria and so forth.

As for such production of target substances by fermentation as described above, it can be said that most of materials used as raw materials are those containing saccharides such as blackstrap molasses. Also in amino acid fermentation or nucleic acid fermentation, culture is performed by using a saccharide as a raw material. Although sugarcane and so forth abundantly contain starch, it is rare to use it as it is as a raw material, but used in most cases as a decomposition product in which starch is decomposed into, for example, monosaccharides or disaccharides. As for the decomposition method, a solution of a saccharifying enzyme such as amylase is generally used, and thereby starch that is polysaccharide is decomposed into relatively low molecular saccharides such as glucose, maltose and maltotriose.

In fermentation using Gram-negative enterobacteria such as *Escherichia coli* (*E. coli*), use of such a starch decomposition solution causes a problem. For example, *E. coli* consumes glucose existing as a main component, but it suffers from the so-called glucose repression, which means that oligosaccharides containing two or more monosacchatides such as maltose are consumed only after monosaccharides are completely consumed. Therefore, if fermentation is terminated when only glucose that is the main component of starch decomposition solution is consumed, oligosaccharides such as maltose are not assimilated but remain vainly. Further, if it is intended to consume oligosaccharides after consumption of glucose, culture time must be extended for that and therefore utility cost and so forth are wasted ineffectively.

It is known that *E. coli* and *Salmonella typhimurium* generally suffer from the glucose repression. That is, when it is intended to assimilate glucose together with other carbon sources such as lactose, maltose and glycerol, glucose is assimilated first and the other carbon sources are assimilated later. Monod et al. discovered that, when lactose and glucose were used as carbon sources, two-phase proliferation, i.e., so-called diauxie, was observed (Monod, J., Growth, 11, 223–247, 1947). Through researches in molecular biology, the mechanism thereof is becoming clear. That is, IIA$^{Glc}$ (glucose PTS enzyme II) that acts as a phosphate donor for glucose in the phosphate cascade at the time of assimilation in the glucose-phosphoenolpyruvate-sugar phosphotransferase system, i.e., so-called PTS system, exists in a dephosphorylated state. The dephosphorylated IIA$^{Glc}$ causes the so-called inducer exclusion, in which the dephosphorylated IIA$^{Glc}$ inhibits uptake of the other saccharides (Postma P. W., Lengeler J. W. and Jacobson G. R.: in *Escherichia coli* and *Salmonella:* Cellular and Molecular Biology (ed. Neidhardt F. C.), pp. 1149–1174, 1996, ASM Press, Washington D.C.).

Uptake of maltose in *E. coli* suffers form the glucose repression, and this is caused by the interaction between the dephosphorylated IIA$^{Glc}$ and the MalK protein that constitutes the uptake system for maltose by non-PTS. That is, when the bacterium is taking up glucose, IIA$^{Glc}$ excessively exists in the cell, and it binds to the MalK protein to inhibit the uptake of maltose. Further, a mutant strain showing improved uptake of maltose in the presence of glucose analogue was also obtained, and it is known that this mutant strain has a mutation in the malK gene coding for the MalK protein (Dean D. A. et al., Regulation of the Maltose Transport System of *Escherichia coli* by the Glucose-specific Enzyme III of the Phosphoenolpyruvate-Sugar Phosphotransferase System., J. Biol. Chem., 265 (34), 21005–21010, 1990; Kuhnau, S. et al., The Activities of the *Escherichia coli* MalK Protein in Maltose Transport and Regulation, and Inducer Exclusion Can Be Separated by Mutations, J. Bacteriol., 173 (7), 2180–2186, 1991).

Further, also for IIA$^{Glc}$, there was reported a mutant strain that contained a mutant protein showing reduced binding with lactose permease (Zeng, G. A. et al., Mutation alanalysis of the enzyme IIIGlc of the phosphoenolpyruvate phosphotransferase system in *Escherichia coli*, Res. Microbiol., 143, 251–261, 1992). The lactose permease is an uptake enzyme for lactose that is one of the non-PTS saccharides.

However, it is unknown whether the aforementioned mutant strains assimilate maltose simultaneously in the presence of glucose.

SUMMARY OF THE INVENTION

An object of the present invention is to improve assimilation ability of a microorganism for oligosaccharides, in particular, maltose, in production of a substance by fermentation utilizing the microorganism with a carbon source containing glucose and oligosaccharides such as starch decomposition solutions.

The inventors of the present invention assiduously studied in order to achieve the aforementioned object. As a result, they found that a microorganism in which an interaction between IIA$^{Glc}$ protein of glucose PTS and a protein involved in non-PTS uptake of maltose was reduced or eliminated could assimilate maltose even in the presence of glucose, and accomplished the present invention.

That is, the present invention provides the followings.

(1) A method for producing a target substance utilizing a microorganism and comprising culturing the microorganism in a medium to produce and accumulate the target substance in the medium and collecting the target substance from the culture, wherein the microorganism is a mutant or recombinant strain of a microorganism in which maltose assimilation is controlled by an interaction between IIA$^{Glc}$ protein of glucose PTS and a protein involved in non-PTS uptake of maltose, and the interaction between IIA$^{Glc}$ protein and a protein involved in non-PTS uptake of maltose of the mutant or recombinant strain is reduced or eliminated, and the strain can take up glucose and maltose.

(2) The method according to (1), wherein the protein involved in non-PTS uptake of maltose is a maltose carrier protein having an ATP decomposition activity.

(3) The method according to (2), wherein the protein is MalK protein.

(4) The method according to any one of (1)–(3), wherein the interaction between IIA$^{Glc}$ protein of glucose PTS and the protein involved in non-PTS uptake of maltose is reduced or eliminated because the MalK protein contained in the microorganism has a mutation selected from a mutation for substituting a Thr residue for the Ala residue at a position of 124 and a mutation for substituting a Gln residue for the Leu residue at a position of 327.

(5) The method according to any one of (1)–(4), wherein the interaction between IIA$^{Glc}$ protein of glucose PTS and the protein involved in non-PTS uptake of maltose is reduced or eliminated because the IIA$^{Glc}$ protein contained in the microorganism has a mutation selected from a mutation for substituting a Ser residue for the Gly residue at a position of 47 and a mutation substituting a Thr residue for the Ala residue at a position of 76.

(6) The method according to any one of (1)–(5), wherein the target substance is an L-amino acid.

(7) The method according to (6), wherein the target substance is selected from the group consisting of L-lysine, L-threonine and L-phenylalanine.

(8) The method according to any one of (1)–(7), wherein the microorganism is an *Escherichia* bacterium.

According to the present invention, assimilation ability of a microorganism for oligosaccharide, in particular, maltose, can be improved in production of a substance by fermentation using the microorganism with a carbon source containing glucose and an oligosaccharide such as starch decomposition solution.

PREFERRED EMBODIMENTS OF THE INVENTION

Figure 1:
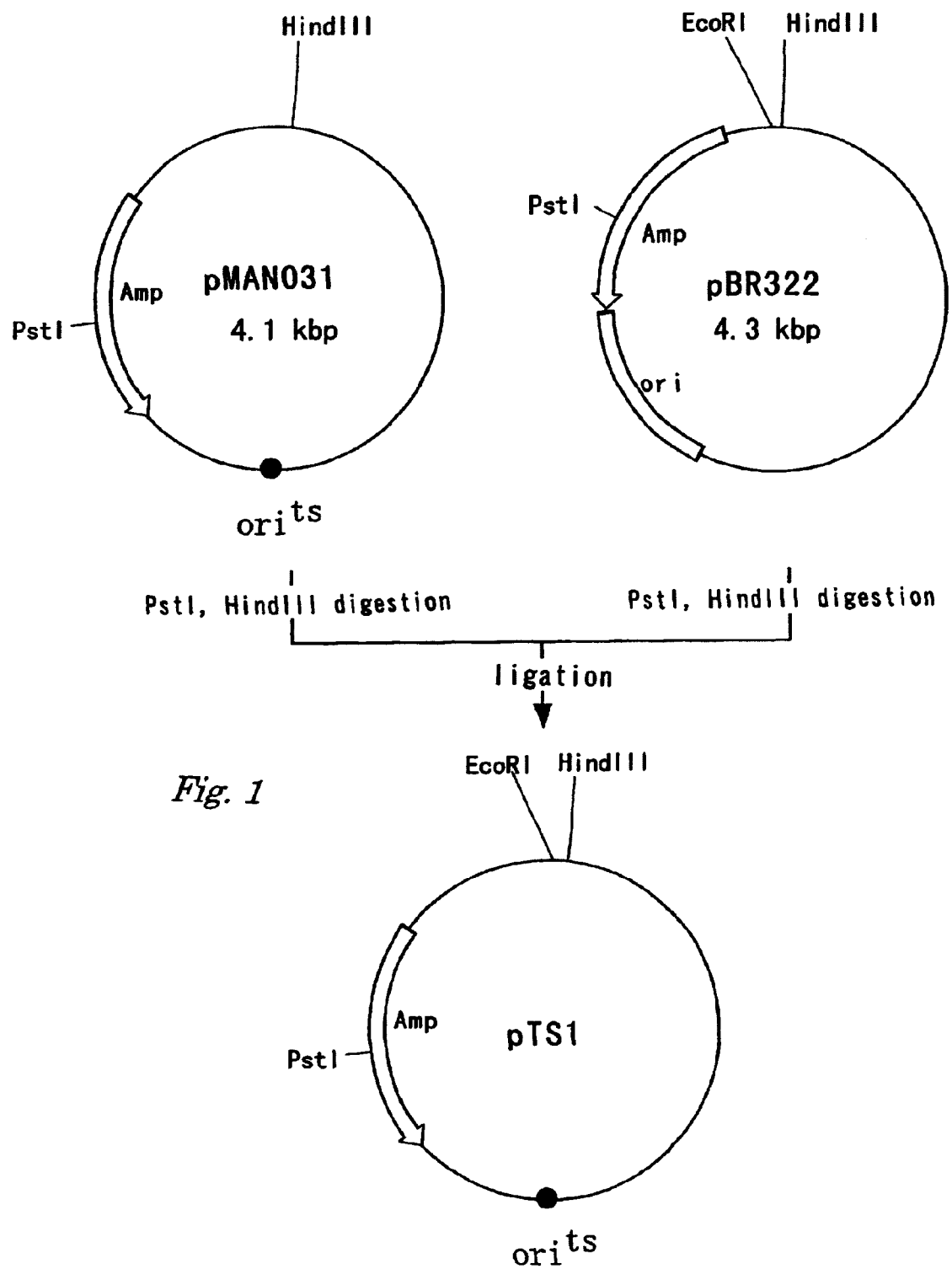
FIG. 1 shows the structure of the plasmid vector pTS1 having a temperature sensitive replication origin.

Hereafter, the present invention will be explained in detail.

The target substance produced by the microorganism according to the present invention may be selected from various L-amino acids including, for example, L-threonine, L-lysine, L-glutamic acid, L-leucine, L-isoleucine, L-valine, L-phenylalanine and so forth. Particularly preferred L-amino acids are L-lysine, L-threonine and L-phenylalanine. In addition, the target substance may be any of substances that have conventionally been produced by microorganisms using a medium containing glucose and an oligosaccharide such as maltose as carbon sources, and may be a nucleic acid such as guanylic acid and inosinic acid, vitamin, antibiotic, growth factor, bioactive substance or the like. The present invention can of course be used for any other substances so long as the substances require a carbon source in the biosynthesis thereof, even if they are not currently produced by using a microorganism.

The microorganism used in the present invention is a microorganism in which maltose assimilation is controlled by an interaction between IIA$^{Glc}$ protein of glucose PTS and a protein involved in non-PTS uptake of maltose. Specifically, there can be mentioned bacteria belonging to the group of enterobacteria such as *Escherichia* bacteria, *Enterobacter* bacteria and *Klebsiella* bacteria, coryneform bacteria, *Bacillus* bacteria, *Serratia* bacteria and so forth. It is preferably a microorganism that allows gene substitution. Whether a microorganism can be used for the present invention or not can be determined by, for example, observing growth of a wild strain of the microorganism in a medium containing glucose and maltose as carbon sources and confirming if the two-phase proliferation, i.e., the so-called diauxie, is observed or not. If diauxie is observed, it is considered that the maltose assimilation should be controlled by an interaction of the IIA$^{Glc}$ protein of glucose PTS and a protein involved in the non-PTS uptake of maltose.

Specific examples of microorganisms that can be used for the present invention include, for example, *Escherichia coli* AJ11442 (NRRL B-12185 and FERM BP-1543, refer to U.S. Pat. No. 4,346,170), *Brevibacterium lactofermentum* AJ3990 (ATCC31269, refer to U.S. Pat. No. 4,066,501) etc. for L-lysine as the target substance, *Escherichia coli* VKPM B-3996 (RIA1867, refer to U.S. Pat. No. 5,175,107), *Corynebacterium acetoacidophilum* AJ12318 (FERM BP-1172, refer to U.S. Pat. No. 5,188,949) etc. for L-threonine, *Escherichia coli* AJ12604 (FERM BP-3579, refer to the European Patent Publication No. 488,424), *Brevibacterium lactofermentum* AJ12637 (FERM BP-4160, refer to French Patent Publication No. 2,686,898) etc. for L-phenylalanine, *Escherichia coli* AJ12624 (FERM BP-3853, refer to French Patent Publication No. 2,680,178), *Brevibacterium lactofermentum* AJ12475 (FERMBP-2922, refer to U.S. Pat. No. 5,272,067) etc. for L-glutamic acid, *Escherichia coli* AJ11478 (FERM P-5274, refer to Japanese Patent Publication (Kokoku) No. 62-34397), *Brevibacterium lactofermentum* AJ3718 (FERM P-2516, refer to U.S. Pat. No. 3,970,519) etc. for L-leucine, *Escherichia coli* KX141 (VKPM B-4781, refer to the European Patent Publication No. 519,113), *Brevibacterium flavum* AJ12149 (FERM BP-759, refer to U.S. Pat. No. 4,656,135) etc. for L-isoleucine, *Escherichia coli* VL1970 (VKPM B-4411, refer to the European Patent Publication No. 519,113), *Brevibacterium lactofermentum* AJ12341 (FERM BP-1763, refer to U.S. Pat. No. 5,188,948) etc. for L-valine and so forth.

Further, when the target substance is L-lysine, L-threonine or L-phenylalanine, strains obtained by introducing a plasmid pVIC40, pCABD2 or pMGAL1, which are incorporated with a gene involved in the production of each of the amino acids, into *E. coli* W3100 (tyrA) can also be suitably used, and they are described in the examples mentioned later.

Furthermore, in the microorganism used for the present invention, activity of a protein involved in production of the target substance may be enhanced, or activity of a protein involved in decomposition or the like of the target substance may be reduced, depending on the target substance.

The microorganism used for the present invention is a mutant strain or recombinant strain obtained from such a microorganism as described above as a parent strain, in which the interaction between IIA$^{Glc}$ protein of glucose PTS and a protein involved in non-PTS uptake of maltose is reduced or eliminated, but it is a microorganism that can take up glucose and maltose. That is, in the present invention, the IIA$^{Glc}$ protein and the protein involved in non-PTS uptake of maltose contain a mutation that does not substantially affect the uptake of glucose and maltose, even though it reduces or eliminates the interaction between them.

In *Escherichia coli*, the IIA$^{Glc}$ protein is encoded by crr gene. Further, as a protein involved in the non-PTS uptake of maltose, the MalK protein can be mentioned, which is encoded by malK gene in *Escherichia coli*.

In order to reduce or eliminate the interaction of the IIA$^{Glc}$ protein and the protein involved in non-PTS uptake of maltose, a mutation that reduce or eliminate the interaction between these proteins can be introduced into one or both of genes coding for these proteins.

A crr gene or malK gene that has such a mutation as mentioned above can be obtained by, for example, isolating crr gene or malK gene from a mutant strain that can grow in a medium containing maltose as a carbon source and a glucose analogue such as 2-deoxyglucose. As a mutant type malK gene that can be obtained as described above, there is known a mutant type malK gene having a mutation for substituting a Thr residue for the 124th Ala residue of the encoded MalK protein (Dean, D. A. et al., J. Biol. Chem., 265 (34), 21005–21010, 1990; Kuhnau, S. et al., J. Bacteriol., 173 (7), 2180–2186, 1991). Further, a mutant type malK gene encoding MalK protein and having a mutation for substituting a Gln residue for the 327th Leu residue (L327Q type mutation), which was obtained by the inventors of the present invention, can also be suitably used for the present invention. Furthermore, a mutant type malK gene encoding a mutant type MalK protein having both of a mutation for substituting a Thr residue for the 124th Ala residue and a mutation for substituting a Gln residue for the 327th Leu residue can also be used for the present invention.

On the other hand, an example of the mutant type crr gene is a crr gene containing a mutation for substituting a Ser residue for the 47th Gly residue of the encoded IIA$^{Glc}$ protein, a mutation for substituting a Thr residue for the 76th Ala residue, or both of these mutations.

The positions of the aforementioned mutations are numbered from the Met residue corresponding to the initiation codon, which is taken as the first codon. In addition, the malK gene or crr gene may contain one or more mutations other than the mutations according to the present invention, and hence deletion, substitution or insertion of one or more amino acid residues may occur in the encoded MalK protein or IIA$^{Glc}$ protein. Even such a malK gene or crr gene may be used for the present invention, so long as the interaction between the MalK protein and IIA$^{Glc}$ protein is reduced or eliminated, and the uptake of glucose and maltose is not substantially affected. When the MalK protein or IIA$^{Glc}$ protein contains deletion or insertion of one or more amino acid residues, the positions of the aforementioned mutations should change. For example, if the MalK protein includes deletion of one amino acid residue on the N-terminus side of the 327th Leu residue, the 327th Leu residue should become the 326th residue. Even in such a case, the 326th Leu residue corresponds to the 327th Leu residue of a wild-type protein. Therefore, in the present specification, the positions of mutations shall represent positions corresponding to the positions in a wild-type gene or wild-type protein.

As the method for introducing the aforementioned mutations into the malK gene and/or crr gene, there can be mentioned a method of introducing a target mutation into the malK gene and/or crr gene by the site-specific mutagenesis or the like to produce a mutant type gene and substituting the obtained mutant type gene for malK gene and/or crr gene on a chromosome of microorganism through gene substitution utilizing homologous recombination.

Such gene substitution can be performed, for example, in the same manner as the gene substitution using a temperature-sensitive plasmid described later. Examples of the temperature-sensitive plasmid of *Escherichia coli* include pMAN031 (J. Bacteriol., 162, 1196, 1985), pMAN997 (WO99/03988) and so forth. These plasmids can autonomously replicate in *Escherichia coli* at least at 30° C., but cannot autonomously replicate at 37–42° C.

Further, a mutant strain having a target mutation in the malK gene and/or crr gene can also be obtained by treating a microorganism by UV irradiation or with a mitagenizing agent used for usual mutagenesis treatment such as N-methyl-N'-nitro-N-nitrosoguanidine (NTG) or nitrous acid and selecting a strain that can grow in a medium containing a glucose analogue such as 2-deoxyglucose.

Whether an obtained candidate strain is a target mutant strain or not can be confirmed by isolating malK gene or crr gene from the candidate strain and investigating its nucleotide sequence around the mutation point.

As the medium used for culture of the microorganism of the present invention, conventionally used well-known media can be used depending on the kind of the microorganism to be used. That is, usual media containing a carbon source, nitrogen source, inorganic ions and other organic components as required can be used. However, it is preferable to use a medium containing glucose and an oligosaccharide such as maltose as carbon sources.

As the carbon source other than glucose and maltose, sugars such as lactose, galactose and starch hydrolysate, alcohols such as glycerol and sorbitol, organic acids such as fumaric acid, citric acid and succinic acid and so forth can be used.

As the nitrogen source, inorganic ammonium salts such as ammonium sulfate, ammonium chloride and ammonium phosphate, organic nitrogen such as soybean hydrolysate, ammonia gas, aqueous ammonia and so forth can be used.

As organic trace nutrient source, appropriate amounts of required substances such as vitamin B$_1$, L-homoserine and L-tyrosine, yeast extract and so forth are preferably contained. In addition to these, small amounts of potassium phosphate, magnesium sulfate, iron ions, manganese ions and so forth are added as required.

Culture may be performed under well-known conditions that are conventionally used depending on the microorganism to be used. For example, culture is preferably performed under an aerobic condition for 16–120 hours. Culture temperature is controlled to be 25–45° C. and pH is controlled to be 5–8 during the culture. Inorganic or organic acidic or alkaline substances as well as ammonia gas and so forth can be used for pH adjustment.

To collect a metabolic product from a medium after completion of the culture, no special method is required for the present invention. That is, collection of the target substance can be attained by a combination of well-known methods such as those using an ion exchange resin, precipitation and others.

BEST MODE FOR CARRYING OUT THE INVENTION

Hereafter, the present invention will be explained more specifically with reference to the following examples. The reagents used in the following examples were obtained from Wako Pure Chemicals or Nakarai Tesque unless otherwise indicated. The compositions of the media used in each example are shown below.

| [L medium] | |
|---|---|
| Bacto tryptone peptone (DIFCO) | 10 g/L |
| Yeast extract (DIFCO) | 5 g/L |
| NaCl | 5 g/L |

These were autoclaved at 120° C. for 20 minutes.

| [L agar medium] | |
|---|---|
| L medium | |
| Bacto agar (DIFCO) | 15 g/L |

These were steam-sterilized at 120° C. for 20 minutes.

| [SOC medium] | |
|---|---|
| Bacto tryptone peptone (DIFCO) | 20 g/L |
| Yeast extract (DIFCO) | 5 g/L |
| 10 mM NaCl | |
| 2.5 mM KCl | |
| 10 mM MgSO$_4$ | |
| 10 mM MgCl$_2$ | |
| 20 mM Glucose | |

The components except for magnesium solution and glucose were autoclaved (120° C., 20 minutes), then added with 2 M magnesium stock solution (1 M MgSO$_4$, 1 M MgCl$_2$) and 2 M glucose solution, which solutions had been preliminarily passed through a 0.22 μm filter, and passed through a 0.22 μm filter again.

| [M9 minimal medium] | |
|---|---|
| Na$_2$HPO$_4$.12H$_2$O | 80 g/L |
| KH$_2$PO$_4$ | 15 g/L |
| NaCl | 2.5 g/L |
| NH$_4$Cl | 5 g/L |
| MgSO$_4$.7H$_2$O | 246.48 mg/L |
| Saccharide (glucose or maltose or mixture of these at a suitable ratio) | 5 g/L |
| pH 7.0 | |

MgSO$_4$ and glucose were separately sterilized (120° C., 20 minutes) and added. A suitable amount of amino acids and vitamins were added as required. pH was adjusted with NaOH.

| [M9 minimal agar medium] | |
|---|---|
| M9 minimal medium | |
| Bacto agar (DIFCO) | 15 g/L |

| [Amino acid production medium] | |
|---|---|
| (NH$_4$)$_2$SO$_4$ | 20 g/L |
| KH$_2$PO$_4$ | 1 g/L |
| MgSO$_4$.7H$_2$O | 1 g/L |
| FeSO$_4$.7H$_2$O | 10 mg/L |
| MnSO$_4$.4H$_2$O | 10 mg/L |
| Yeast Extract (DIFCO) | 2 g/L |
| Saccharide (glucose or maltose or mixture of these at a suitable ratio) | 40 g/L |
| L-Tyrosine | 100 mg/L |
| CaCO$_3$ (Japanese pharmacopoeia) | 30 g/L |
| Streptomycin | 50 mg/L. |

The saccharide, MgSO$_4$.7H$_2$O and streptomycin were separately sterilized. The other components were mixed, adjusted to pH 7.0 with KOH and autoclaved at 115° C. for 10 minute. CaCO$_3$ was subjected to dry sterilization at 180° C. for 2 days. Streptomycin was sterilized by filtration.

EXAMPLE 1

Introduction of Mutation into MalK Gene and Confirmation of Improvement in Maltose Assimilation Property A colony of *E. coli* W3100 was inoculated into 5 ml of L medium and cultured overnight with shaking. From the obtained cells, chromosomal DNA was prepared by using Wizard Genomic DNA Purification Kit (Promega). PCR was performed by using the above chromosomal DNA as a template and the primers shown below.

[Primer 1]
5'-GGCGGTAATGTGGAGATGCGCACATAAAATCGCC (SEQ ID NO:1)
-3'

[Primer 2]
5'-CCTGAGTCATTGCTTTTCTTTTTTCACATCACCT (SEQ ID NO:2)
GTGAC-3'

PCR was performed by using Pyrobest DNA Polymerase produced by Takara Shuzo and according to the protocol attached to the enzyme. After completion of the reaction, the amplification product was blunt-ended and phosphorylated by using BKL Kit produced by Takara Shuzo. The amplified fragment was ligated by using Ligation Kit ver.2 (Takara Shuzo) to pSTV28 (Takara Shuzo) treated with a restriction enzyme Sma I (Takara Shuzo) and then dephosphorylated. This ligation reaction mixture was transformed into *E. coli* JM109 according to the method of Hanahan et al. (Hanahan, D., Studies on transformation of *Escherichia coli* with plamids, J. Mol. Biol., 166, 557–580, 1983). Selection of the transformants was carried out on L agar medium containing 50 μg/ml of chloramphenicol (Cm), 0.2 mM IPTG (Isopropyl-1-thio-β-D-galactopyranoside) and 40 μg/ml of X-gal (5-bromo-4-chloro-3-indolyl-β-D-galactopyranoside). A plasmid was extracted from the transformants in a conventional manner, and the nucleotide sequence of the inserted fragment was determined to confirm that the malK gene was inserted into the Sma I site of pSTV28. This plasmid was designated as pSTVmalK.

Nucleotide substitution of the MalK gene on pSTVmalK was carried out as follows. It was decided to introduce substitution of A for G as the nucleotide at the 370th position (substitution of Thr for the 124th Ala residue in the MalK protein). The positions in DNA nucleotide sequences used herein are numbered from A of the initiation codon, ATG, which was taken as the first nucleotide, and the positions of amino acid residues are numbered form the Met residue corresponding to the above initiation codon, which was taken as the first amino acid residue.

First, substitution of the nucleotide on the plasmid was performed by using QuickChange™ Site-Directed Mutagenesis Kit (STRATAGENE). The sequences of the primers used for introducing the malK mutation are shown below.

[Primer 3]
5'-CGGAAGTGCTACAACTGACGCATTTGCTGGATCG (SEQ ID NO:3)
C-3'

[Primer 4]
5'-GCGATCCAGCAAATGCGTCAGTTGTAGCACTTCC (SEQ ID NO:4)
G-3'

The introduction of the mutation was confirmed by determining the nucleotide sequence of the concerned site according to the protocol attached to the kit. The produced plasmid was designated as pSTVmalK-A124T. The plasmid was digested with restriction enzymes EcoR I and Hind III (all produced by Takara Shuzo) and ligated to the same restriction enzyme sites of a plasmid vector pTS1 having a temperature sensitive replication origin.

pTS1 was obtained by exchanging Pst I-Hind III fragments of pMAN031 (Matsuyama, S. and Mizushima S., Construction and characterization of a deletion mutation lacking micF, a proposed regulatory gene for OmpF synthesis in *Escherichia coli*., J. Bacteriol., 162 (3), 1196–1202, 1985) and pBR322 (produced by Takara Shuzo) (FIG. 1). The produced plasmid was designated as pTSmalK-A124T.

Homologous recombination of the malK gene with malK on the chromosome of *E. coli* W3100 (tyrA) (see Europe Patent Publication No. 488,424) according to a usual procedure for homologous recombination (Matsuyama, S and Mizushima, S., J. Bacteriol., 162(3), 1196–1202, 1985) utilizing the temperature sensitivity of the aforementioned plasmid pTSmalK-A124T.

Briefly, *E. coli* W3100 (tyrA) was transformed by the method of Hanahan et al. (J. Mol. Biol., 166, 557–580) using pTSmalK-A124T. A colony emerged after culture at 30° C. was inoculated into 5 ml of L medium containing 50 µg/ml ampicillin in a test tube and cultured at 30° C. overnight with shaking. This culture broth was diluted $10^3$ to $10^4$ times, and 0.1 ml of the dilution was applied to L agar medium containing 50 µg/ml of ampicillin and cultured overnight at 42° C. An emerged colony was inoculated into 5 ml of L medium contained in a test tube and cultured overnight at 30° C. with shaking. This culture broth in a volume of 0.1 ml was inoculated into 5 ml of L medium contained in a test tube and cultured at 37–42° C. for 3–4 hours with shaking. This culture broth was diluted $10^3$ to $10^7$ times, and 0.1 ml of the dilution was applied to L agar medium and cultured overnight at 37–42° C. The ampicillin sensitivity of an emerged colony was confirmed.

The mutation point of the target gene-substituted strain was confirmed as follows. PCR was performed by using the aforementioned colony as a template and Pyrobest DNA Polymerase. Primer 1 and Primer 2 were used as the primers, and PCR was performed according to the protocol attached to the enzyme. After completion of the reaction, the reaction mixture was subjected to gel filtration with the purpose of removing residual primers in the reaction mixture. The used column was MicroSpin™ S-400HR Column (produced by Amersham Pharmacia Biotech), and the procedure was according to the protocol attached to the column. The obtained PCR product was a mutant type malK gene of the malK gene-substituted strain. The nucleotide sequence of this gene was determined mainly for the region containing the mutation point. The mutant strain confirmed to be introduced with the desired mutation into the malK gene as desired was designated as *E. coli* W3100 (tyrA)malK1.

Growth of *E. coli* W3100 (tyrA)malK1 in a medium consisting of M9 medium added with 0.05% glucose and 0.45% maltose was monitored by OD measurement. *E. coli* W3100 (tyrA) was used as a control. Although the two-phase proliferation, i.e., the so-called diauxie, was observed for *E. coli* W3100 (tyrA), such two-phase proliferation was not observed for the malK mutation-introduced strain, *E. coli* W3100 (tyrA)malK1. That is, it was found that, because of the introduction of the malK mutation, the inducer exclusion was not caused and maltose was assimilated simultaneously with the glucose assimilation.

EXAMPLE 2

Introduction of Mutation into crr Gene and Confirmation of Improvement in Maltose Assimilation Property In this example, it was decided to introduce a mutation into the crr gene in order to reduce the interaction between the MalK protein and the crr gene product, $IIA^{Glc}$.

A colony of *E. coli* W3100 was inoculated into 5 ml of L medium and cultured overnight with shaking. From the obtained cells, chromosomal DNA was prepared by using Wizard Genomic DNA Purification Kit (Promega). PCR was performed by using the above chromosomal DNA as a template and the primers shown below.

[Primer 5]
5'-GATTTCTTTAGTATCGGCACCAATGATTTAACGC-3'    (SEQ ID NO: 5)
[Primer 6]
5'-AAATTGCCGCGATCTAGACAGTGCCATTGC-3'    (SEQ ID NO: 6)

PCR was performed by using Pyrobest DNA Polymerase produced by Takara Shuzo and according to the protocol attached to the enzyme. After completion of the reaction, the amplification product in the reaction mixture was blunt-ended and phosphorylated by using BKL Kit produced by Takara Shuzo. The obtained amplified fragment was ligated by using Ligation Kit ver.2 (Takara Shuzo) to pMW219 (Nippon Gene) that was treated with a restriction enzyme SmaI (Takara Shuzo) and then dephosphorylated. *E. coli* JM109 was transformed with this ligation reaction mixture according to the method of Hanahan et al. Selection of the transformants was carried out on L agar medium containing 25 µg/ml of kanamycin (Km), 0.2 mM IPTG (Isopropyl-1-thio-β-D-galactopyranoside) and 40 µg/ml of X-gal (5-bromo-4-chloro-3-indolyl-β-D-galactopyranoside). A plasmid was extracted from the transformants in a conventional manner, and the nucleotide sequence of the inserted fragment was determined to confirm that the crr gene was inserted into the Sma I site of pMW219. This plasmid was designated as pMWcrr.

Nucleotide substitution of the crr gene on pMWcrr was carried out as follows. It was decided to introduce nucleotide substitution of A for the G at the 226th position (substitution of Thr for the 76th Ala residue, Zeng, G. A. et al., Mutational analysis of the enzyme III$^{Glc}$ of the phosphoenolpyruvate phosphotransferease system in Escherichia coli., Res. Microbiol., 143, 251–261, 1992). The positions in DNA nucleotide sequences used herein are numbered from A of the initiation codon, ATG, which was taken as the first nucleotide, and the positions of amino acid residues are numbered form the Met residue corresponding to the above initiation codon, which was taken as the first amino acid residue.

First, substitution of the nucleotide on the plasmid was performed by using QuickChange™ Site-Directed Mutagenesis Kit (STRATAGENE). The sequences of the primers used for introducing the crr mutation are shown below.

[Primer 7]
5'-GAAACCAACCACACATTCTCTATCGAATCTGATA (SEQ ID NO:7)
                                     GCGGCG-3'

[Primer 8]
5'-CGCCGCTATCAGATTCGATAGAGAATGTGTGGTT (SEQ ID NO:8)
                                     GGTTTC-3'

The introduction of the mutation was confirmed by determining the nucleotide sequence of the concerned site according to the protocol attached to the aforementioned kit. The produced plasmid was designated as pMWcrr-A76T. The plasmid was digested with restriction enzymes EcoR I and Xba I (both produced by Takara Shuzo) and ligated between the same restriction enzyme sites of the plasmid vector pMAN997 (refer to International Patent Publication WO99/03988) having a temperature sensitive replication origin.

The produced plasmid was designated as pMANcrr-A76T. Homologous recombination was performed for crr gene on E. coli W3100 (tyrA) chromosome using this plasmid by the same method as that used for obtaining the malK mutant strain, and thus a strain introduced with the mutation into the crr gene was obtained.

The mutation point of the target gene-substituted strain was confirmed in the same manner as the case of obtaining the malK mutant strain. PCR was performed by using an ampicillin-resistant colony as a template and Ex Taq Polymerase (produced by Takara Shuzo). Primer 5 and Primer 6 were used as the primers, and PCR was performed according to the protocol attached to the enzyme. After completion of the reaction, the reaction mixture was subjected to gel filtration with the purpose of removing residual primers in the reaction mixture. The used column was MicroSpin™ S-400HR Column (produced by Amersham Pharmacia Biotech), and the procedure was according to the protocol attached to the column. The obtained PCR product was a mutant type crr gene of the crr gene-substituted strain. The nucleotide sequence of this gene was determined mainly for the region containing the mutation point. The mutant strain that was confirmed to be introduced with the desired mutation as described above was designated as E. coli W3100 (tyrA)crr3.

Growth of E. coli W3100 (tyrA)crr3 in a medium consisting of M9 medium added with 0.05% glucose and 0.45% maltose was monitored by OD measurement. E. coli W3100 (tyrA) was used as a control. Although the two-phase proliferation, i.e., the so-called diauxie, was observed for coli W3100 (tyrA), such two-phase proliferation was not observed for the crr mutation-introduced strain, E. coli W3100 (tyrA)crr3. That is, it was found that, because of the introduction of crr mutation, the inducer exclusion was not caused and maltose was assimilated simultaneously with the glucose assimilation. The same event was observed when nucleotide substitution of A for the 139th G (substitution of Ser for the 47th Gly residue) was introduced.

EXAMPLE 3

Acquisition of Glucose Analogue-Resistant Strain, Identification of Mutation Point of the Resistant Strain and Introduction of the Mutation into E. coli W3100 (tyrA)

A colony of E. coli W3100 (tyrA) was inoculated into 5 ml of L medium contained in a test tube and cultured overnight with shaking. The cultured cells were washed twice with 5 ml of physiological saline and suspended in the same volume of physiological saline. This suspension was applied in an amount of 0.1 ml to M9 agar medium containing maltose as a carbon source and the surface was dried. One platinum loop of 2-deoxyglucose was placed on the plate, and the cells were cultured at 37° C. for two or three days. E. coli W3100 (tyrA) can utilize maltose as a carbon source, but if a glucose analogue such as 2-deoxyglucose exists, it suffers from the repression and becomes unable to grow. In this case, a growth inhibition circle is formed around the point where the glucose analogue is placed as the center. If culture is performed for two or three days, colonies that can grow emerge at a certain frequency in the inhibition circle. Glucose analogue-resistant strains were obtained based on the above phenomenon.

Mutations on the malK gene of malK#1 and malK#2 were investigated among the glucose analogue-resistant strains. The mutation points were confirmed as follows. A colony of each strain was formed, and PCR was performed by using the colony as a template and Pyrobest DNA Polymerase. PCR was performed by using Primer 1 and Primer 2 as the primers and according to the protocol attached to the enzyme. After completion of the reaction, the reaction mixture was subjected to gel filtration with the purpose of removing residual primers in the reaction mixture. The used column was MicroSpin™ S-400HR Column (produced by Amersham Pharmacia Biotech), and the procedure was according to the protocol attached to the column. The obtained PCR products were malK genes of the glucose-resistant strains malK#1 and malK#2, and the nucleotide sequences of these genes were determined. As a result, it was found that a substituted for the 980th T in the both strains, and in connection with that, Gln was substituted for the 327th Leu residue. This is a mutation that has not been known so far. This mutation was designated as L327Q type mutation.

The L327Q type mutation was introduced into E. coli W3100 (tyrA) by the method described above. The obtained mutation-introduced strain was designated as E. coli W3100 (tyrA)malK327. In a similar manner, growth of E. coli W3100 (tyrA)malK327 in a medium consisting of M9 medium added with 0.05% glucose and 0.45% maltose was monitored by OD measurement. E. coli W3100 (tyrA) was used as a control. Although the two-phase proliferation, i.e., the so-called diauxie, was observed for E. coli W3100 (tyrA), such two-phase proliferation was not observed for the malK mutation-introduced strain, E. coli W3100 (tyrA) malK327. That is, it was found that, because of the introduction of the novel malK mutation, the inducer exclusion was not caused and maltose was assimilated simultaneously with the glucose assimilation.

EXAMPLE 4

Evaluation of L-Amino Acid Productivity of malK Mutant Strains pVIC40 (WO90/04636), pCABD2 (WO95/16042) and pMGAL1 (Japanese Patent Laid-open Publication (Kokai) No. 5-344881) were each introduced into E. coli W3100 (tyrA)malK327, and abilities to produce L-lysine, L-threonine and L-phenylalanine were investigated for each strain.

pVIC40 is a plasmid containing the threonine operon and can be prepared from E. coli VKPM B-3996 strain (deposited at USSR Antibiotics Research Institute (VNIIA) with a registration number of RIA1867) harboring the plasmid (WO90/04636).

pCABD2 contains DNA (dapA*24) coding for dihydrodipicolinate synthase (DDPS) derived from Escherichia coli and having a mutation for eliminating the feedback inhibition by L-lysine, DNA (lysC*80) coding for aspartokinase III derived from Escherichia coli and having a mutation for eliminating the feedback inhibition by L-lysine, DNA (dapB) coding for dihydrodipicolinate reductase derived from Escherichia coli, and DNA (ddh) coding for diaminopimelate dehydrogenase derived from Brevibacterium lactofermentum (WO95/16042).

pMGAL1 contains a gene coding for 3-deoxy-D-arabinohepturonate-7-phosphate synthase derived from Escherichia bacterium of which feedback inhibition was eliminated, and a gene coding for chorismate mutase-prephenate dehydratase derived from Escherichia bacterium of which feedback inhibition is eliminated (Japanese Patent Laid-open Publication No. 5-344881).

E. coli W3100 (tyrA)malK327 was transformed with each plasmid by the method of Hanahan et al. Each obtained transformant was inoculated into 5 ml of L medium containing 50 µg/ml of streptomycin and cultured at 37° C. overnight with shaking. Then, the culture broth was applied in an amount of 50 µl to L agar medium containing 50 µg/ml of streptomycin and cultured overnight at 37° C. An amino acid production medium containing a mixture of glucose and maltose (36 g/L glucose, 5.8 g/L of maltose) as the carbon source in a volume of 20 ml was introduced into a 500-ml volume Sakaguchi flask, and ⅛ of the cells grown on the aforementioned agar medium was scraped and inoculated into the medium. After completion of the culture, concentration of each amino acid and remained glucose and maltose were quantified. As controls, transformants obtained by introducing each of the plasmids into E. coli W3100 (tyrA) were used. The results are shown in Table 1.

TABLE 1

| strain (host/plasmid) | Lys (g/L) | Thr (g/L) | Phe (g/L) | Remained glucose (g/L) | remained maltose (g/L) |
|---|---|---|---|---|---|
| W3110(tyrA)/pRS | 0.00 | 0.00 | 0.91 | 0.0 | 5.8 |
| W3110(tyrA)malK327/pRS | 0.00 | 0.00 | 0.86 | 0.0 | 0.0 |
| W3110(tyrA)/pCABD2 | 9.55 | — | — | 0.0 | 5.6 |
| W3110(tyrA)malK327/pCABD2 | 10.80 | — | — | 0.0 | 0.0 |
| W3110(tyrA)/pVIC40 | — | 8.48 | — | 0.0 | 4.1 |
| W3110(tyrA)malK327/pVIC40 | — | 8.62 | — | 0.0 | 0.0 |
| W3110(tyrA)/pMGAL1 | — | — | 4.57 | 0.0 | 5.7 |
| W3110(tyrA)malK327/pMGAL1 | — | — | 4.69 | 1.2 | 0.0 |

—: Not tested, pRS: vector (initial concentrations of glucose and maltose were 36 g/L and 5.8 g/L, respectively, and culture time was 14 hours)
Lys: lysine; Thr: threonine; Phe: phenylalanine When E. coli W3100 (tyrA) was used as the host, maltose was not assimilated yet when glucose was consumed. On the other hand, when E. coli W3100 (tyrA)malK327 was used as the host, maltose was assimilated within a similar culture time, and thus it was found that consumption of maltose was not suffered from the glucose repression.

Further, the E. coli W3100 (tyrA)malK327 strains harboring each of pVIC40, pCABD2 and pMGAL1 showed improved L-lysine, L-threonine and L-phenylalanine producing abilities compared with the E. coli W3100(tyrA) strains harboring each of the plasmids.

What is claimed is:

1. A method for producing a target substance utilizing a microorganism comprising culturing the microorganism in a medium containing glucose and an oligosaccharide, allowing said substance to accumulate in the medium, and collecting said target substance from the medium, wherein the microorganism is a mutant or recombinant strain of a microorganism in which maltose assimilation is controlled by an interaction between $IIA^{Glc}$ protein of glucose PTS and MalK, and wherein said interaction in the mutant or recombinant strain is reduced or eliminated because said MalK protein has a mutation selected from the group consisting of substituting a Thr residue for the Ala residue at the position corresponding to position 124 in E. coli MalK and substituting a Gln residue for the Leu residue at the position corresponding to position 327 in E. coli MalK; and/or said $IIA^{Glc}$ protein has a mutation selected from the group consisting of substituting a Ser residue for the Gly residue at the position corresponding to position 47 in E. coli $IIA^{Glc}$ protein and substituting a Thr residue for the Ala residue at the position corresponding to position 76 in E. coli $IIA^{Glc}$ protein;

and wherein said strain can take up glucose and maltose.

2. The method according to claim 1, wherein the oligosaccharide is maltose.

3. The method according to claim 1 or 2, wherein said target substance is an L-amino acid.

4. The method according to claim 3, wherein said target substance is selected from the group consisting of L-lysine, L-threonine and L-phenylalanine.

5. The method according to claim 1 or 2, wherein said microorganism is an Escherichia bacterium.

* * * * *

UNITED STATES PATENT AND TRADEMARK OFFICE
CERTIFICATE OF CORRECTION

| | | |
|---|---|---|
| PATENT NO. | : 7,097,999 B2 | Page 1 of 1 |
| APPLICATION NO. | : 10/121693 | |
| DATED | : August 29, 2006 | |
| INVENTOR(S) | : Tsujimoto et al. | |

Figure 2:
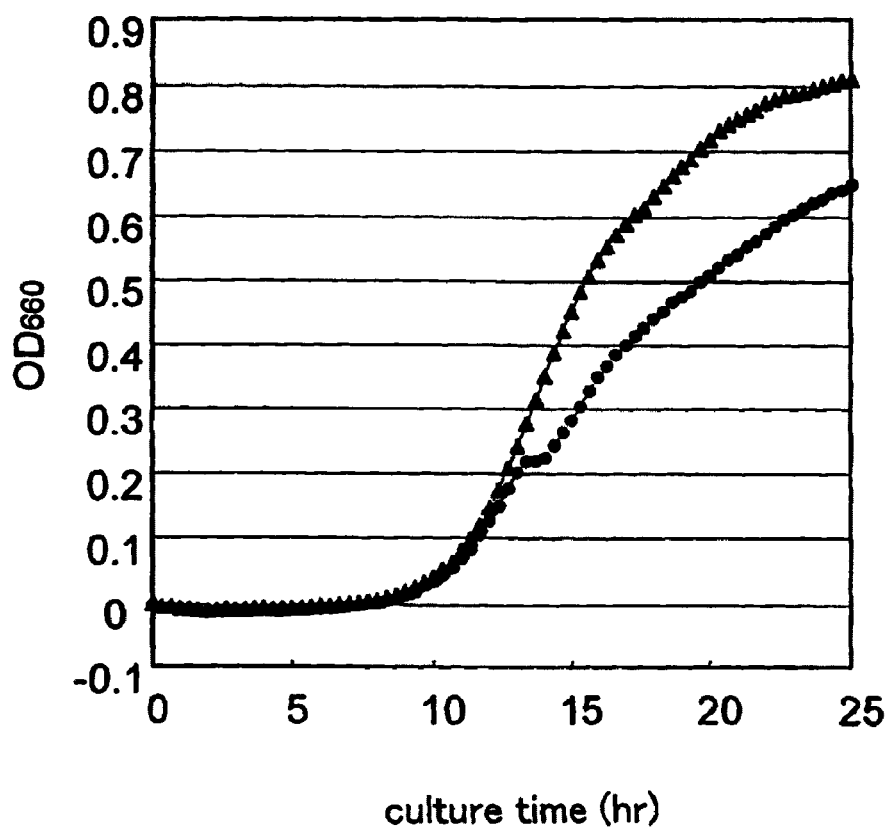
FIG. 2 shows growth of *E. coli* W3100 (tyrA)crr3 in a medium containing glucose and maltose.
Figure 3:
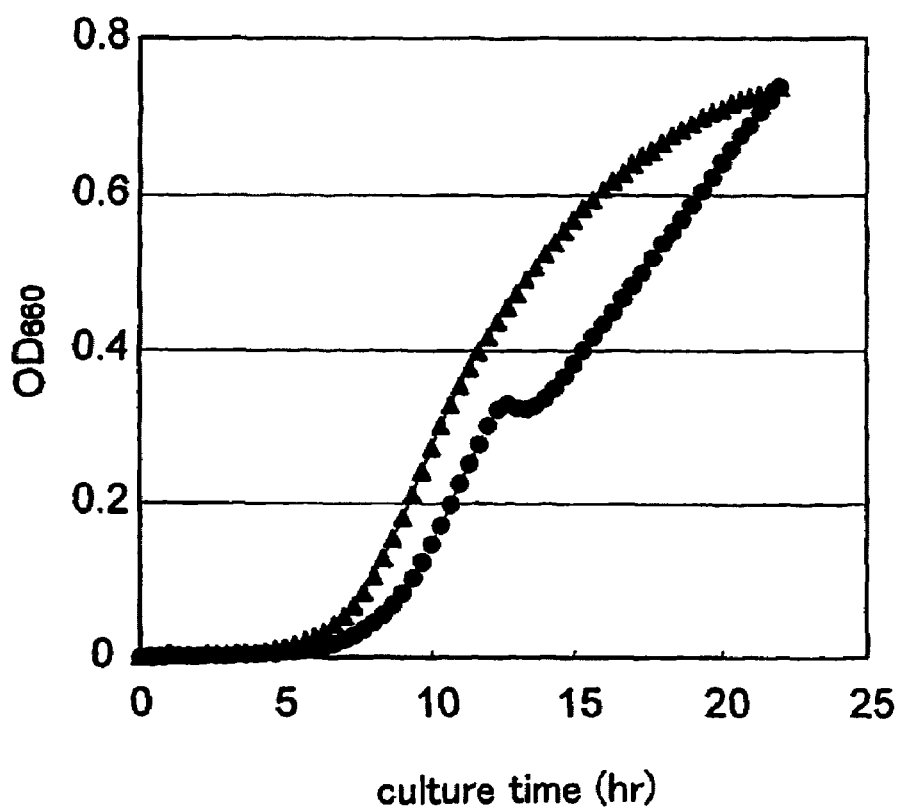
FIG. 3 shows growth of *E. coli* W3100 (tyrA)malK327 in a medium containing glucose and maltose.

It is certified that error appears in the above-identified patent and that said Letters Patent is hereby corrected as shown below:

In The Drawings
Delete drawing sheets 2 and 3 containing FIGURES 2 and 3.

In column 3 of the issued patent, delete the brief descriptons of FIGS. 2 and 3, appearing at paragraphs 4 and 5 as indicated below:

"FIG. 2 shows growth of *E. coli* W3100 (tyrA)crr3 in a medium containing glucose and maltose."

"FIG. 3 shows growth of *E. coli* W3100 (tyrA)mal K327 in a medium containing glucose and maltose."

Signed and Sealed this

Twenty-sixth Day of June, 2007

JON W. DUDAS
*Director of the United States Patent and Trademark Office*

SEQUENCE LISTING

<160> NUMBER OF SEQ ID NOS: 8

<210> SEQ ID NO 1
<211> LENGTH: 34
<212> TYPE: DNA
<213> ORGANISM: Artificial Sequence
<220> FEATURE:
<223> OTHER INFORMATION: Artificial DNA

<400> SEQUENCE: 1
ggcggtaatg tggagatgcg cacataaaat cgcc                       34

<210> SEQ ID NO 2
<211> LENGTH: 39

```
<212> TYPE: DNA
<213> ORGANISM: Artificial Sequence
<220> FEATURE:
<223> OTHER INFORMATION: Artificial DNA

<400> SEQUENCE: 2
cctgagtcat tgcttttctt ttttcacatc acctgtgac                               39

<210> SEQ ID NO 3
<211> LENGTH: 35
<212> TYPE: DNA
<213> ORGANISM: Artificial Sequence
<220> FEATURE:
<223> OTHER INFORMATION: Artificial DNA

<400> SEQUENCE: 3
cggaagtgct acaactgacg catttgctgg atcgc                                   35

<210> SEQ ID NO 4
<211> LENGTH: 35
<212> TYPE: DNA
<213> ORGANISM: Artificial Sequence
<220> FEATURE:
<223> OTHER INFORMATION: Artificial DNA

<400> SEQUENCE: 4
gcgatccagc aaatgcgtca gttgtagcac ttccg                                   35

<210> SEQ ID NO 5
<211> LENGTH: 34
<212> TYPE: DNA
<213> ORGANISM: Artificial Sequence
<220> FEATURE:
<223> OTHER INFORMATION: Artificial DNA

<400> SEQUENCE: 5 gatttctttα gtatcggcac caatgattta acgc                                    34

<210> SEQ ID NO 6
<211> LENGTH: 30
<212> TYPE: DNA
<213> ORGANISM: Artificial Sequence
<220> FEATURE:
<223> OTHER INFORMATION: Artificial DNA

<400> SEQUENCE: 6
aaattgccgc gatctagaca gtgccattgc                                         30

<210> SEQ ID NO 7
<211> LENGTH: 40
<212> TYPE: DNA
<213> ORGANISM: Artificial Sequence
<220> FEATURE:
<223> OTHER INFORMATION: Artificial DNA

<400> SEQUENCE: 7
gaaaccaacc acacattctc tatcgaatct gatagcggcg                              40

<210> SEQ ID NO 8
<211> LENGTH: 40
<212> TYPE: DNA
<213> ORGANISM: Artificial Sequence
<220> FEATURE:
<223> OTHER INFORMATION: Artificial DNA
```

```
<400> SEQUENCE: 8
cgccgctatc agattcgata gagaatgtgt ggttggtttc                              40
```